US008923483B2

(12) United States Patent
Schneider

(10) Patent No.: US 8,923,483 B2
(45) Date of Patent: Dec. 30, 2014

(54) ROTATION OF AN X-RAY IMAGE ON A DISPLAY

(75) Inventor: Charles Schneider, Pittsford, NY (US)

(73) Assignee: Carestream Health, Inc., Rochester, NY (US)

(*) Notice: Subject to any disclaimer, the term of this patent is extended or adjusted under 35 U.S.C. 154(b) by 358 days.

(21) Appl. No.: 13/488,477

(22) Filed: Jun. 5, 2012

(65) Prior Publication Data
US 2013/0322600 A1 Dec. 5, 2013

(51) Int. Cl.
H05G 1/08 (2006.01)
H05G 1/64 (2006.01)
G09G 5/30 (2006.01)
G09G 5/34 (2006.01)

(52) U.S. Cl.
USPC .......... 378/98.5; 378/163; 378/210; 378/901; 345/641; 345/650

(58) Field of Classification Search
CPC ............ G09G 5/00; G09G 5/14; G09G 5/22; G09G 5/30; G09G 5/32; G09G 5/38; G09G 5/42; H04N 1/0035; H04N 1/00352; H04N 1/00405; H04N 1/00404; H04N 1/00411; H04N 1/00413; H04N 1/0044; H04N 1/00469; G06F 3/00; G06F 3/01; G06F 3/017; G06F 3/012; G06F 3/013; G06F 3/02; G06F 3/033; G06F 3/0338; G06F 3/048; G06F 3/0481; G06F 3/0484; G06F 3/04845; G06F 3/14; A61B 5/74; A61B 5/742; A61B 5/7425; A61B 5/743; A61B 5/7435; G06T 1/00; G06T 1/0007; G06T 3/00; G06T 3/40; G06T 3/60; G06T 3/604; G06T 3/606; G06K 9/20

USPC .......... 378/91, 98, 98.2, 98.5, 162, 163, 204, 378/210, 901; 382/128, 131, 132, 154, 276, 382/293, 296–298, 325; 345/418, 619, 629, 345/632, 634, 636, 641, 649–661, 664–671, 345/689
See application file for complete search history.

(56) References Cited

U.S. PATENT DOCUMENTS

| | | | |
|---|---|---|---|
| 6,177,937 B1 * | 1/2001 | Stockham et al. | 715/807 |
| 6,266,453 B1 * | 7/2001 | Hibbard et al. | 382/294 |
| 6,638,223 B2 | 10/2003 | Lifshitz et al. | |
| 2006/0026521 A1 * | 2/2006 | Hotelling et al. | 715/702 |
| 2008/0084430 A1 * | 4/2008 | Sakakura | 345/649 |
| 2009/0220174 A1 | 9/2009 | Saito | |
| 2011/0060986 A1 | 3/2011 | Yang | |
| 2011/0102464 A1 * | 5/2011 | Godavari | 345/650 |
| 2013/0069987 A1 * | 3/2013 | Choe | 345/649 |
| 2013/0137974 A1 * | 5/2013 | Sakaguchi et al. | 600/424 |

OTHER PUBLICATIONS

Internet web site, Villamor, Willis, Wroblewski, "Touch Gesture Reference Guide" from on-line source http://www.lukew.com/ff/entry.asp?1071, Apr. 2010. pp. 1-12, printed from WW web on Apr. 14, 2012.

(Continued)

Primary Examiner — Anastasia Midkiff

(57) ABSTRACT

A method for controlling the angular orientation of an x-ray image on a display for a viewer displays at least one rotation mode selector on the display. A viewer instruction selects the rotation mode. An overlay displays with the x-ray image, wherein the overlay provides a center of rotation. A viewer instruction identifies a point lying outside the center of rotation. The image is rotated on the display about the center of rotation according to the identified point.

15 Claims, 4 Drawing Sheets

(56) References Cited

OTHER PUBLICATIONS

Internet web site for gestureworks.com, single page accessed under "Features", entitled "gestureworks in Action" from on-line source http://gestureworks.com/gestureworks-in-action/2011/09/animal-comparison-tool/, developer Ideum, 1 page, printed from WW web on Apr. 14, 2012.

Internet web site for Advantech, single page accessed under "Product News", entitled "Advantech Launches PIT-1503W, Full-flat Patient Terminal at Intelligent Planet & Internet of Things Expo", Oct. 24, 2011. From on-line source http://www.advantech-embedded.com/applied-computing-systems/Infotainment/news.aspx?doc_id={D17BE533-AB79-4860-AA2A-0FFB63EC000, printed from the WW web on Apr. 14, 2012, 1 page.

* cited by examiner

ROTATION OF AN X-RAY IMAGE ON A DISPLAY

FIELD OF THE INVENTION

The present invention relates generally to the field of x-ray image display and more particularly to methods for manipulation of the displayed image by a viewer.

BACKGROUND

The presentation of x-ray image data on a display monitor has a number of advantages over the use of conventional x-ray imaging films. With the x-ray shown on a display monitor, for example, the viewer can adjust characteristics such as image brightness and contrast and perform functions such as pan and zoom that can enhance the usefulness of the image content and can improve assessment and diagnosis of a patient's condition.

Angle of rotation is among the characteristics of an x-ray image that the viewer may want to be able to adjust easily. It can be particularly useful for the practitioner to view an organ or skeletal structure at a preferred reference angle or at a number of different angles in order to more clearly identify and assess problem areas. In some cases, for example, there can be constraints on image detector size and geometry that necessitate imaging of a bone or other structure in a diagonal direction across the detector. The practitioner may find it more useful, however, to view the imaged anatomy in an upright position or at some more natural viewing angle.

There are a number of methods and utilities that enable facile image panning, rotation, zoom, and other manipulation of images on portable displays, such as those provided on hand-held devices, using touch screens. Display monitors for viewing x-ray images, however, are relatively large and are optimized for high resolution and contrast, making it impractical in many cases to provide this type of display with touch screen capability.

Viewer utilities that make image rotation more straightforward and intuitive can be particularly helpful for assisting the radiologist to obtain the view that is best suited for assessing the patient's condition, without requiring complex interaction with the viewing system. The use of on-screen tools that readily perform rotation with a single click or with one operator command can help to improve usability of the viewing system and the overall efficiency of high-volume radiography facilities.

Thus, it can be seen that there is value in providing an operator interface that allows intuitive methods for adjusting the angle of a displayed x-ray on a display screen.

SUMMARY

An object of the present invention is to advance the art of medical imaging by providing ways to manipulate image angle in a straightforward manner, such as with a single click of a mouse button or key. Embodiments of the present invention address the need for an intuitive utility for rotating a displayed x-ray image to any suitable angle that is preferred by a viewing practitioner.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided a method for controlling the angular orientation of an x-ray image on a display for a viewer, the method comprising: displaying at least one rotation mode selector on the display; responding to a viewer instruction that selects the rotation mode by displaying an overlay with the x-ray image, wherein the overlay provides a center of rotation; accepting a viewer instruction that identifies a point lying outside the center of rotation; and rotating the image on the display about the center of rotation according to the identified point.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION

Figure 1:
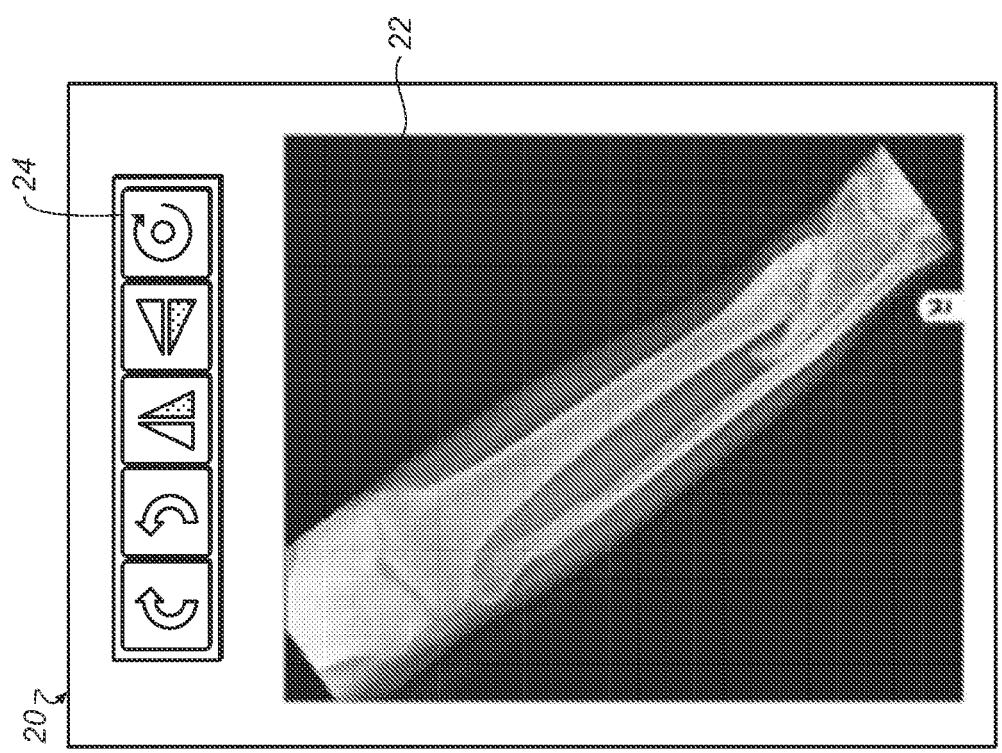
FIG. 1 shows a display with an x-ray image at an oblique orientation.

The following is a detailed description of the preferred embodiments of the invention, reference being made to the drawings in which the same reference numerals identify the same elements of structure in each of the several figures.

Where they are used, the terms "first", "second", and so on, do not necessarily denote any ordinal, sequential, or priority relation, but are simply used to more clearly distinguish one element or set of elements from another, unless specified otherwise. In the context of the present disclosure, the terms "viewer", "operator", and "user" are considered to be equivalent and refer to the viewing practitioner or other person who views and manipulates an x-ray image on a display monitor.

The term "highlighting" for a displayed feature has its conventional meaning as is understood to those skilled in the information and image display arts. In general, highlighting uses some form of localized display enhancement to attract the attention of the viewer. Highlighting a portion of an image on a display, such as an individual organ, bone, or structure, for example, can be achieved in any of a number of ways, including, but not limited to, annotating, displaying a nearby or overlaying symbol, outlining or tracing, display in a different color or at a markedly different intensity or gray scale value than other image or information content, blinking or animation of a portion of a display, or display at higher sharpness or contrast.

Embodiments of the present invention address the need for improved ways to allow image rotation for displayed x-ray images. Where possible, a single click or other viewer action is the only instruction needed to rotate the x-ray image on the display screen, once rotation mode has been selected. This allows rotation in a simple and efficient manner, without requiring the viewer to make a numeric entry or to enter a complex sequence of commands. Referring to FIG. 1, there is shown a display 20 for an exemplary x-ray image 22 of a portion of the lower leg of a patient. Images of this region and of other anatomy may be obtained at an oblique angle relative to the x-ray computed radiography (CR) or film cassette or digital radiography (DR) receiver, due to dimensional constraints, for example. However, the practitioner may prefer to view the anatomy in an upright position. A selector 24 is provided on display 20, such as an icon as shown in the FIG. 1 example. A viewer instruction of some type selects a rotation mode, such as by clicking on selector 24 using a computer mouse or other pointer or using a touch screen selection, for example.

Figure 2:
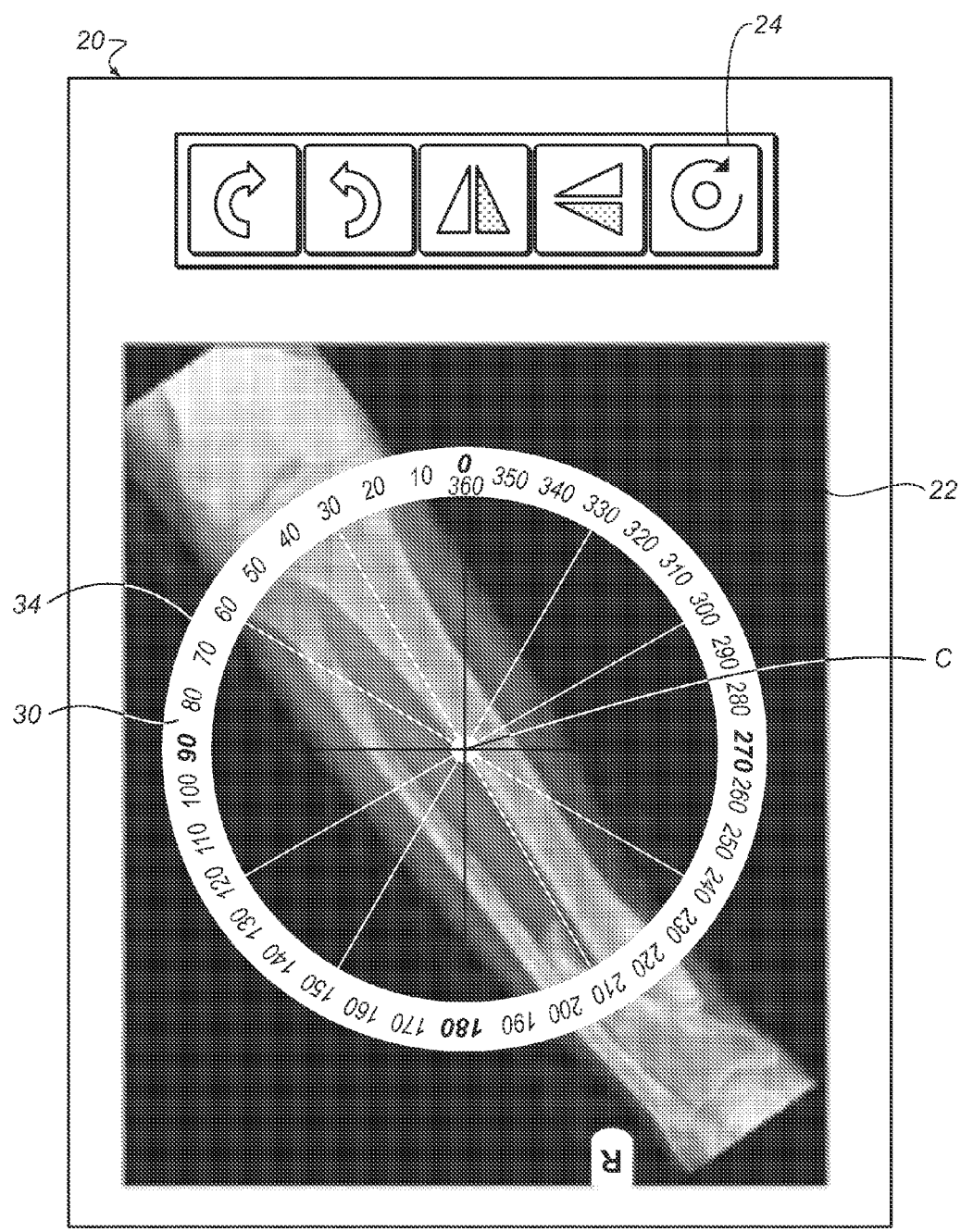
FIG. 2 shows an overlay provided on the display for rotating the underlying image.

FIG. 2 shows system response to viewer selection of rotation mode after clicking on or otherwise actuating selector 24. An overlay 30 is displayed with image 22, and a center of rotation C is identified. In the embodiment shown in FIG. 2, overlay 30 is a compass or other template, with a circular band 34 having optional angular indicia thereon, such as at every 10 degree interval as shown. Other types of overlay could alternately be employed, with or without numerical angular coordinates or explicit identification of center of rotation C. Overlay 30 can be opaque or have some level of at least partial transparency. A variable level of transparency is provided, according to an embodiment of the present invention, so that overlay 30 fades in intensity with successive rotation instructions. Overlay 30 can be circular in outline or may have some other suitable shape. According to an alternate embodiment of the present invention, overlay 30 readjusts after rotation to the new rotation position, so that angle settings are reset, such as with 0 degrees in the top vertical (or "12 o'clock") position as viewed, for example.

Figure 3:
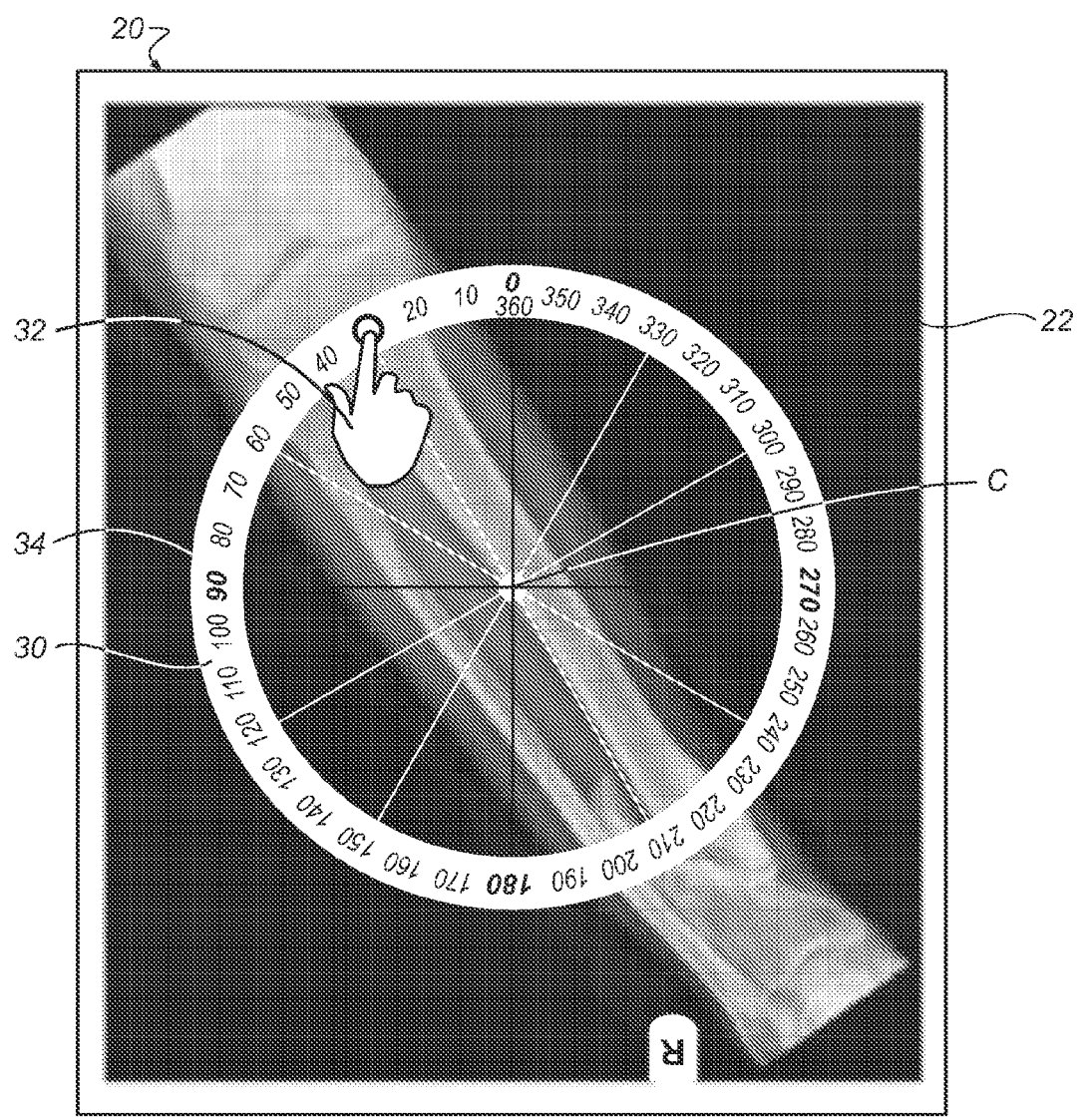
FIG. 3 shows entry of a viewer instruction to rotate the displayed image.

Rotation is executed based on a viewer instruction that identifies a point lying outside of center of rotation C. Referring to FIG. 3, an embodiment of the present invention is shown in which an optional cursor icon 32 is provided, tracking the actual or relative screen position of a mouse or other cursor control device relative to angular indicia on overlay 30. This feature allows the viewer to position a mouse cursor or other type of cursor at any appropriate location within the image for rotation, indicating the amount of rotation that will be provided when a specific point is selected. The cursor does not need to be positioned on circular band 34 of overlay 30; tracking is provided so that a line between the cursor position and center of rotation C extends through circular band 34 and indicates a possible rotation angle. The computer system that controls the display accepts the viewer instruction that identifies a point lying outside the center of rotation and responds by rotating the image on the display about the center of rotation according to the identified point. According to an embodiment of the present invention, identifying a point, such as with a mouse key or button click, causes the image to be rotated so that the identified point is vertically aligned with center point C.

Figure 4:
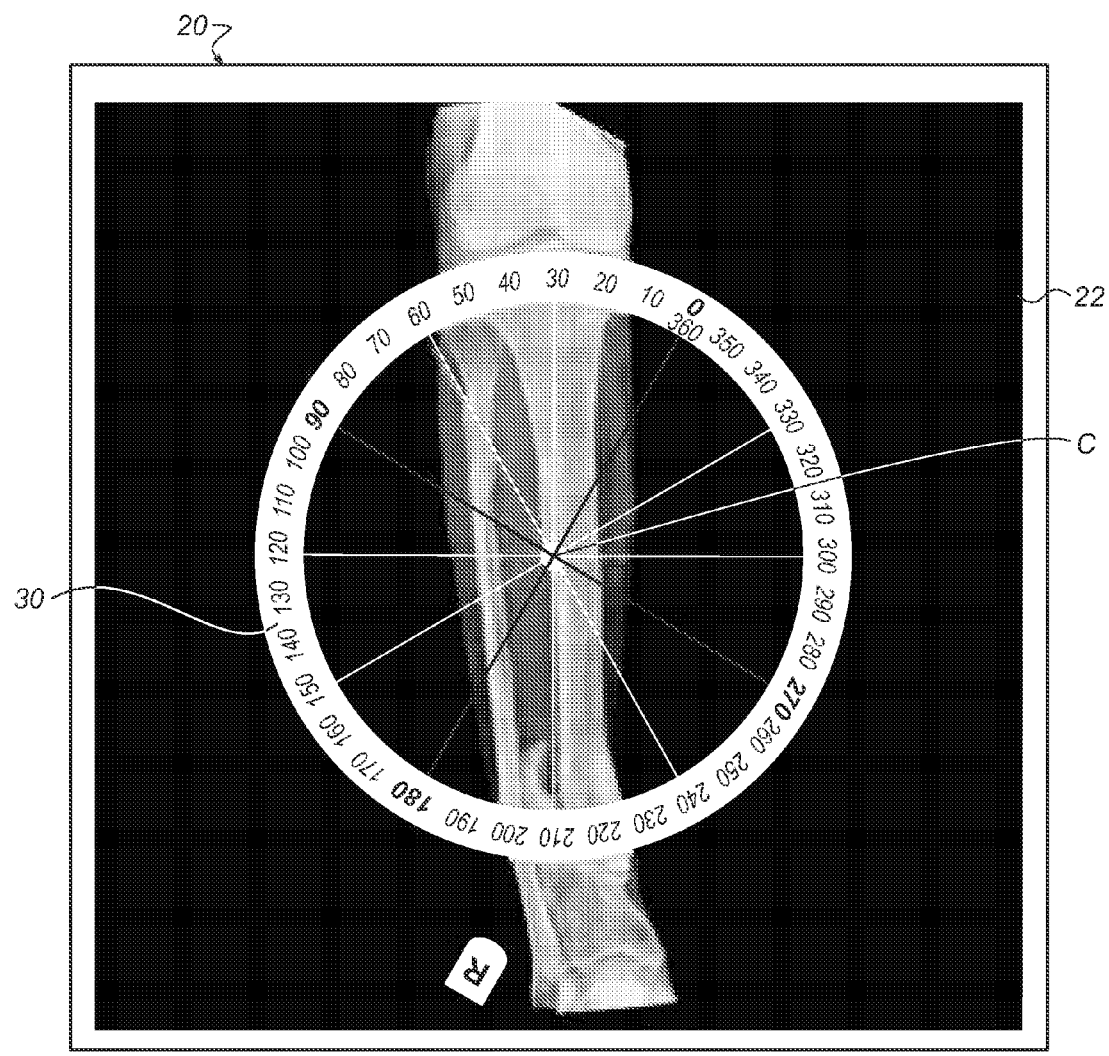
FIG. 4 shows rotation of the image in response to the viewer instruction.

In this way, following identification of a suitable point by the viewer, the image is rotated correspondingly. According to one embodiment of the present invention, the image is rotated so that the indicated point is vertically aligned with the center of rotation C. FIG. 4 shows rotation for the selection shown in the example of FIG. 3. According to an embodiment of the present invention, rotation moves the selected point to the location initially identified as the "0 degree" position, otherwise termed the vertical or "12 o'clock" position. This rotation thus shifts the entire displayed image corresponding to the selected point to a fixed position. With this arrangement, a single click of a mouse key or button or other instruction that identifies a single point is all that is needed for image rotation. Overlay 30 continues to display until the next time the viewer toggles selector 24 (FIGS. 1 and 2), an instruction that explicitly exits rotation mode. According to an alternate embodiment of the present invention, the system automatically exits rotation mode after performing one rotation; overlay 30 is not displayed after the rotate instruction is executed. Adjusting the rotation again requires the viewer to re-select rotation mode.

Overlay 30 can have different behavior according to whether the cursor position is within or outside of the compass or other template shape. According to an embodiment of the present invention, highlighting is used to indicate the amount of incremental movement that will be executed.

Overlay 30 is centered within the image or display area according to embodiments described in FIG. 2 and following. However, it should be noted that additional controls for adjusting the centering of overlay 30 can be provided in an alternate embodiment of the present invention, allowing additional flexibility for rotation of the image. Overlay 30 is shown with indicia that mark every 10 degree increment; alternate marking could be used, as noted earlier, depending on factors such as the available angular resolution and display size. Center of rotation C is clearly marked in the examples shown, but could be unmarked or implicit in an alternate embodiment.

In an alternate embodiment, the single click or other instruction entered by the viewer rotates the image to another position, other than the "upright" or vertical position shown in FIG. 4. Thus, for example, another preferred angle of orientation can be provided, depending on the type of image obtained. Scaling of the image to fit within boundaries of the display following rotation is optional. A "back-up" instruction is also available, allowing the viewer to view previous, successively entered rotation positions.

The selection, click or other instruction entered in rotation mode by the viewer can be performed using a mouse or other pointing device well known to those skilled in the graphical user interface (GUI) arts. In an alternate embodiment, with an image recognition system such as camera coupled to the display screen or computer, gesture analysis or gaze-tracking is used to observe viewer actions or the focus of attention of the viewer and position the cursor icon 32 at a suitable position along overlay 30 accordingly. Instruction entry can be indicated by a keyboard press or mouse click. Alternately, resting of the cursor at a position after a predetermined time interval can be used to send the rotate instruction. According to an alternate embodiment of the present invention, an audible message or signal is sensed in order to enter rotation mode. Audible instructions are then used to provide rotation according to the resolution of overlay angular indicia.

Image processing for embodiments of the present invention is executed on a computer or dedicated logic control processor. In the context of the present disclosure, the terms "processor" and "computer" can be broadly interpreted to describe any type of computer, computer system, or logic processor hardware that is capable of executing programmed instructions for the image processing and display functions described herein. Unless specifically stated otherwise as apparent from the preceding discussion, it is appreciated that throughout the description, discussions utilizing terms such as "accepting instructions", "processing" or "computing" or "calculating" or "determining" or "displaying" or "determining" or the like, refer to the action and processes of a computer system, or workstation or similar electronic computing device that manipulates and transforms data represented as physical (electronic) quantities within the computer system memories or registers or other such information storage, transmission or display devices.

Certain aspects of the present invention include process steps and instructions described herein in the form of algorithms or image processing utilities. It should be noted that the process steps and instructions of the present invention could be embodied in software, firmware or hardware, and when embodied in software, could be downloaded to reside on and be operated from different computer processing platforms used by a variety of operating systems.

The present invention also relates to an apparatus for performing the operations herein. This apparatus may be a processor specially constructed for the required purposes, or it may comprise a general-purpose computer selectively activated or reconfigured by a computer program stored in the computer. Such a computer program may be stored in a computer readable storage medium, such as, but not limited to, any type of disk including magnetic disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus to practice the method according to the present invention. Furthermore, the computer(s) referred to in the specification may include a single processor or may use architectures that employ multiple processors for increased speed and computing capability.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method for controlling the angular orientation of an x-ray image on a display for a viewer, comprising:
    displaying at least one rotation mode selector on the display;
    responding to a viewer instruction that selects the rotation mode by displaying an overlay with the x-ray image, wherein the overlay provides a center of rotation and an angular indicia for the displayed image;
    accepting a viewer instruction that identifies a point lying outside the center of rotation; and
    rotating the image on the display about the center of rotation according to the identified point.

2. The method of claim 1 wherein the viewer instructions are entered using a touch screen.

3. The method of claim 1 wherein one or more of the viewer instructions are entered using a computer mouse, a joystick, or another pointing device that is in signal communication with the display.

4. The method of claim 1 wherein one or more of the viewer instructions are obtained from a gesture or viewer gaze-tracking or from an audible instruction.

5. The method of claim 1 wherein rotating the image comprises rotating the image so that the identified point is rotated to a fixed position.

6. The method of claim 1 wherein the overlay comprises a circular portion.

7. The method of claim 1 wherein the identified point lies on the overlay.

8. The method of claim 1 wherein the identified point is highlighted on the overlay.

9. The method of claim 1 further comprising scaling the image to fit the display according to the rotation.

10. A method for adjusting the angular orientation of an x-ray image on a display for a viewer, comprising:
    displaying at least one rotation mode selector on the display;
    responding to a viewer instruction that selects the rotation mode by displaying an overlay with the x-ray image, wherein the overlay indicates a center of rotation and indicates one or more rotation angles;
    accepting a viewer instruction that identifies a point lying outside the center of rotation;
    rotating the image on the display about the center of rotation according to the identified point;
    fading the intensity of the overlay following rotation of the image; and
    scaling the rotated image to fit the display.

11. The method of claim 10 wherein the viewer instructions are entered using a touch screen.

12. The method of claim 10 wherein one or more of the viewer instructions are entered using a computer mouse, a joystick, or another pointing device that is in signal communication with the display.

13. The method of claim 10 wherein one or more of the viewer instructions are obtained from a gesture or viewer gaze-tracking or from an audible instruction.

14. The method of claim 10 wherein the overlay is removed from the display following rotation of the image.

15. The method of claim 10 wherein the viewer instruction is a single click of a computer mouse key.

* * * * *